US012440841B2

(12) United States Patent
Foster et al.

(10) Patent No.: US 12,440,841 B2
(45) **Date of Patent: *Oct. 14, 2025**

(54) MICROFABRICATED DROPLET DISPENSOR WITH IMMISCIBLE FLUID AND GENETIC SEQUENCER

(71) Applicant: Owl biomedical, Inc., Goleta, CA (US)

(72) Inventors: John S Foster, New Orleans, LA (US); Mehran Hoonejani, Goleta, CA (US); Kevin Shields, Santa Barbara, CA (US); Hansueli Meyer, Acton, MA (US); Robert Pinard, Lowell, MA (US); Matthias Wahl, Solingen (DE)

(73) Assignee: Owl biomedical, Inc., Goleta, CA (US)

( * ) Notice: Subject to any disclaimer, the term of this patent is extended or adjusted under 35 U.S.C. 154(b) by 1184 days.

This patent is subject to a terminal disclaimer.

(21) Appl. No.: 17/324,570

(22) Filed: May 19, 2021

(65) Prior Publication Data

US 2021/0268506 A1 Sep. 2, 2021

Related U.S. Application Data

(63) Continuation-in-part of application No. 16/009,163, filed on Jun. 14, 2018, now Pat. No. 11,040,347.

(51) Int. Cl.

| | |
|---|---|
| ***B01L 3/00*** | (2006.01) |
| ***C12Q 1/6869*** | (2018.01) |

(52) U.S. Cl.

CPC ... *B01L 3/502784* (2013.01); *B01L 3/502738* (2013.01); *B01L 3/502761* (2013.01); *C12Q 1/6869* (2013.01); *B01L 2200/0652* (2013.01); *B01L 2200/0673* (2013.01); *B01L 2300/021* (2013.01); *B01L 2400/0622* (2013.01)

(58) Field of Classification Search

CPC ......... B01L 3/502784; B01L 3/502738; B01L 3/502761; B01L 2200/0652; B01L 2200/0673; B01L 2300/021; B01L 2400/0622; B01L 2300/1861; C12Q 1/6869; C12Q 1/6806

See application file for complete search history.

(56) References Cited

U.S. PATENT DOCUMENTS

| | | | |
|---|---|---|---|
| 9,150,852 | B2 | 10/2015 | Samuels et al. |
| 9,372,144 | B2 | 6/2016 | Foster et al. |
| 9,399,797 | B2 | 7/2016 | Hutchison et al. |
| 9,410,151 | B2 | 8/2016 | Link et al. |
| 9,440,232 | B2 | 9/2016 | Fraden |

(Continued)

FOREIGN PATENT DOCUMENTS

WO WO 2015/173710 A2 11/2015

*Primary Examiner* — Samuel P Siefke
(74) *Attorney, Agent, or Firm* — Jaquelin K Spong

(57) ABSTRACT

A microfabricated droplet dispensing structure is described, which may include a MEMS microfluidic fluidic valve, configured to open and close a microfluidic channel. The opening and closing of the valve may separate a target biological particle containing genomic material, and a bead from a sample stream, and direct these two particle into a single droplet formed at the edge of the substrate. The droplet may then be encased in a sheath flow of an immiscible fluid, and provided to a sequencing module. The sequencing module may sequence the genomic material and/or an identifying barcode attached to the bead.

20 Claims, 10 Drawing Sheets

(56) References Cited

U.S. PATENT DOCUMENTS

| | | | |
|---|---|---|---|
| 11,040,347 | B2 * | 6/2021 | Foster ............... B01L 3/502738 |
| 2012/0194805 | A1 | 8/2012 | Ness et al. |
| 2012/0289428 | A1 | 11/2012 | Duffy et al. |
| 2015/0174576 | A1 | 6/2015 | Van Vilet et al. |
| 2017/0307486 | A1 | 10/2017 | Leck et al. |
| 2018/0154361 | A1 | 6/2018 | Foster et al. |

* cited by examiner

MICROFABRICATED DROPLET DISPENSOR WITH IMMISCIBLE FLUID AND GENETIC SEQUENCER

CROSS REFERENCE TO RELATED APPLICATIONS

This US nonprovisional patent application is a continuation-in-part, claiming priority to U.S. patent application Ser. No. 16/009,163, filed Jun. 14, 2018. This prior application is incorporated by reference in its entirety.

STATEMENT REGARDING FEDERALLY SPONSORED RESEARCH

Not applicable.

STATEMENT REGARDING MICROFICHE APPENDIX

Not applicable.

BACKGROUND

The present invention is directed to a system for the manipulation of particles and biological materials, and forming droplets containing these particles.

Biomedical researchers have for some time perceived the need to work with small quantities of fluid samples, and to identify compounds uniquely within these small volumes. These attributes allow large numbers of experiments to be carried out in parallel, saving time and money on equipment and reagents, and reducing the need of patients to produce large volume samples.

Indeed, the analysis of small fragments of nucleic acids and proteins suspended in small quantities of buffer fluid is an essential element of molecular biology. The ability to detect, discriminate, and utilize genetic and proteomic information allows sensitive and specific diagnostics, as well as the development of treatments. In particular, there is a need to unambiguously identify small quantities of biological material and analytes.

Most genetic and proteomic analysis requires labeling for detection of the analytes of interest. Such labelling may be referred to as "barcoding", suggesting that the label is unique and correlated to some feature or identity. For example, in sequencing applications, nucleotides added to a template strand during sequencing-by-synthesis typically are labeled, or are intended to generate a label, upon incorporation into the growing strand. The presence of the label allows detection of the incorporated nucleotide. Effective labeling techniques are desirable in order to improve diagnostic and therapeutic results.

At the same time, precision manipulation of streams of fluids with microfluidic devices is revolutionizing many fluid-based technologies. Networks of small channels are a flexible platform for the precision manipulation of small amounts of fluids. The utility of such microfluidic devices depends critically on enabling technologies such as the microfluidic pumps and valves, electrokinetic pumping, dielectrophoretic pump or electrowetting driven flow. The assembly of such modules into complete systems provides a convenient and robust way to construct microfluidic devices.

However, virtually all microfluidic devices are based on flows of streams of fluids; this sets a limit on the smallest volume of reagent that can effectively be used because of the contaminating effects of diffusion and surface adsorption. As the dimensions of small volumes shrink, diffusion becomes the dominant mechanism for mixing leading to dispersion of reactants. This is a large and growing area of biomedical technology, as indicated by a growing number of issued patents in the field.

U.S. Pat. No. 9,440,232 describes microfluidic structures and methods for manipulating fluids and reactions. The structures and methods involve positioning fluid samples, e.g., in the form of droplets, in a carrier fluid (e.g., an oil, which may be immiscible with the fluid sample) in predetermined regions in a microfluidic network. In some embodiments, positioning of the droplets can take place in the order in which they are introduced into the microfluidic network (e.g., sequentially) without significant physical contact between the droplets. Because of the little or no contact between the droplets, there may b$^e$ little or no coalescence between the droplets. Accordingly, in some such embodiments, surfactants are not required in either the fluid sample or the carrier fluid to prevent coalescence of the droplets.

U.S. Pat. No. 9,410,151 provides microfluidic devices and methods that are useful for performing high-throughput screening assays and combinatorial chemistry. This patent provides for aqueous based emulsions containing uniquely labeled cells, enzymes, nucleic acids, etc., wherein the emulsions further comprise primers, labels, probes, and other reactants. An oil based carrier-fluid envelopes the emulsion library on a microfluidic device. Such that a continuous channel provides for flow of the immiscible fluids, to accomplish pooling, coalescing, mixing, Sorting, detection, etc., of the emulsion library.

U.S. Pat. No. 9,399,797 relates to droplet based digital PCR and methods for analyzing a target nucleic acid using the same. In certain embodiments, a method for determining the nucleic acid make-up of a sample is provided.

U.S. Pat. No. 9,150,852 describes barcode libraries and methods of making and using them including obtaining a plurality of nucleic acid constructs in which each construct comprises a unique N-mer and a functional N-mer and segregating the constructs into a fluid compartments such that each compartment contains one or more copies of a unique construct None of these references uses a small, micromechanical valving structure to control the volume of fluid surrounding the barcoded item, and to select the particle enclosed in the droplet. Accordingly, the droplets cannot be made "on demand", and cannot be made to enclose a particle which is the object of the study.

SUMMARY

Accordingly, it was the object of the invention to provide a microfabricated system that can separate target particles from non-target material, also separate a labelled bead, and combine the two particles in a single droplet. In addition to the target particle and the bead, the droplet may comprise a first aqueous fluid, such as a saline or buffer fluid. The droplet may be dispensed into a stream of a second fluid, immiscible with the first fluid. Thus, the droplet may maintain its integrity as a single, discrete, well defined unit because the fluids are immiscible and the droplets do not touch or coalesce.

When the target particle is a biological material such as a cell, with antigens located on its outer surface, the target particle may become attached to the bead by conjugation of these antigens with antibodies disposed on the bead. The bead may further be labelled by an identifying fluorescent signature, which may be a plurality of fluorescent tags affixed to the bead. Accordingly, each target cell, now bound to an identifiable, labelled fluorescent bead, may be essentially barcoded for its own identification. This may allow a large number of experiments to be performed on a large population of such droplets, encased in the immiscible fluid, because the particles are all identifiable and distinguishable.

In some embodiments, a genetic sequencer may be coupled to the MEMS device, which may sequence the genetic material contained in the biological particle.

Accordingly, a microfabricated droplet dispensing structure is described, which may include a MEMS micromechanical fluidic valve, configured to open and close a microfluidic channel. The opening and closing of the valve may separate a target particle and/or a bead from a fluid sample stream, and direct these two particles into a single droplet. The droplet may then be encased in a sheath of an immiscible fluid and delivered to a downstream receptacle or exit.

The system may further comprise a fluid sample stream flowing in the microfluidic channel, wherein the fluid sample stream comprises target particles and non-target material, and an interrogation region in the microfluidic channel. Within the interrogation region, the target particle may be identified among non-target material, and the microfabricated MEMS fluidic valve may separate the target particle from the non-target material in response to a signal from the interrogation region, and direct the target particle into the droplet.

The system may also make use of a bead attached to a plurality of fluorescent tags, wherein the fluorescent tags specify the identity of the bead with a fluorescent signal, and wherein the microfabricated MEMS fluidic valve is configured to separate the bead and direct the bead into the droplet, wherein the bead and a target particle, are located within the same droplet.

In some embodiments, a genetic sequencer may be coupled to the MEMS device and MEMS fluidic valve, which may sequence the genetic material contained in the biological particle. The sequencer may make use of next generation sequencing techniques, including cDNA libraries, and rolling circle amplification, as described in detail below.

BRIEF DESCRIPTION OF THE DRAWINGS

Various exemplary details are described with reference to the following figures, wherein.

It should be understood that the drawings are not necessarily to scale, and that like numbers may refer to like features.

DETAILED DESCRIPTION

Figure 1:
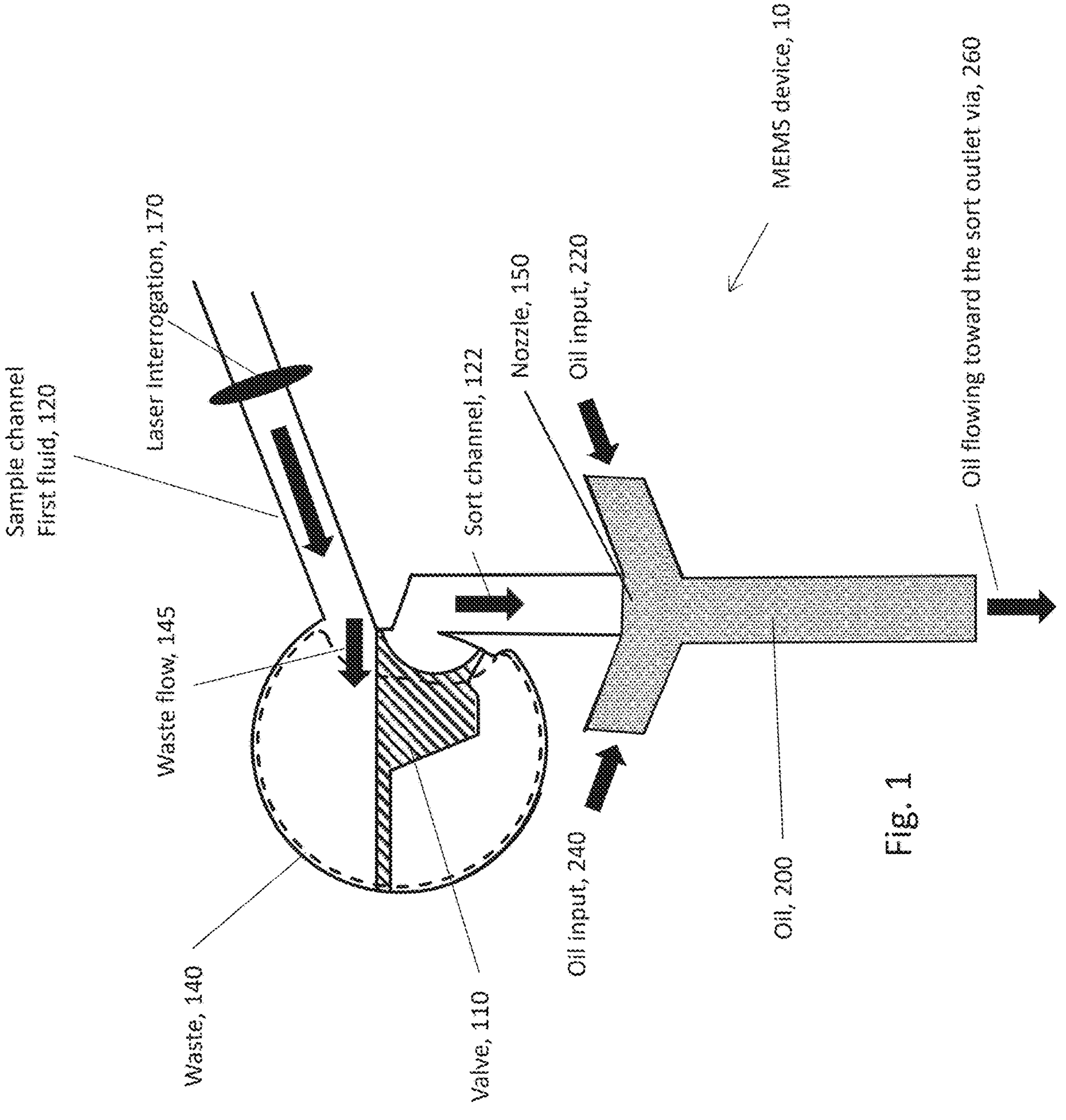
FIG. 1 is a schematic illustration of an embodiment of a microfabricated droplet dispenser with an immiscible fluid with the microfabricated MEMS fluidic valve in the closed position.

The following discussion presents a plurality of exemplary embodiments of the novel microfabricated droplet dispensing system. The following reference numbers are used in the accompanying figures to refer to the following:

110 microfabricated MEMS valve
120 fluid input channel
122 sort channel
140 waste channel
150 nozzle
170 interrogation region
145 non-sort flow
200 oil
220 oil input 1
240 oil input 2
260 oil flowing to outlet via
300 water droplet in oil
310 bead in water droplet
320 target particle in water droplet
400 laser heater
500 merging area The system includes a microfabricated droplet dispenser that dispenses the droplets into an immiscible fluid. The system may be applied to a fluid sample stream, which may include target particles as well as non-target material. The target particles may be biological in nature, such as biological cells like T-cells, tumor cells, stem cells, for example. The non-target material might be plasma, platelets, buffer solutions, or nutrients, for example.

Figure 2:
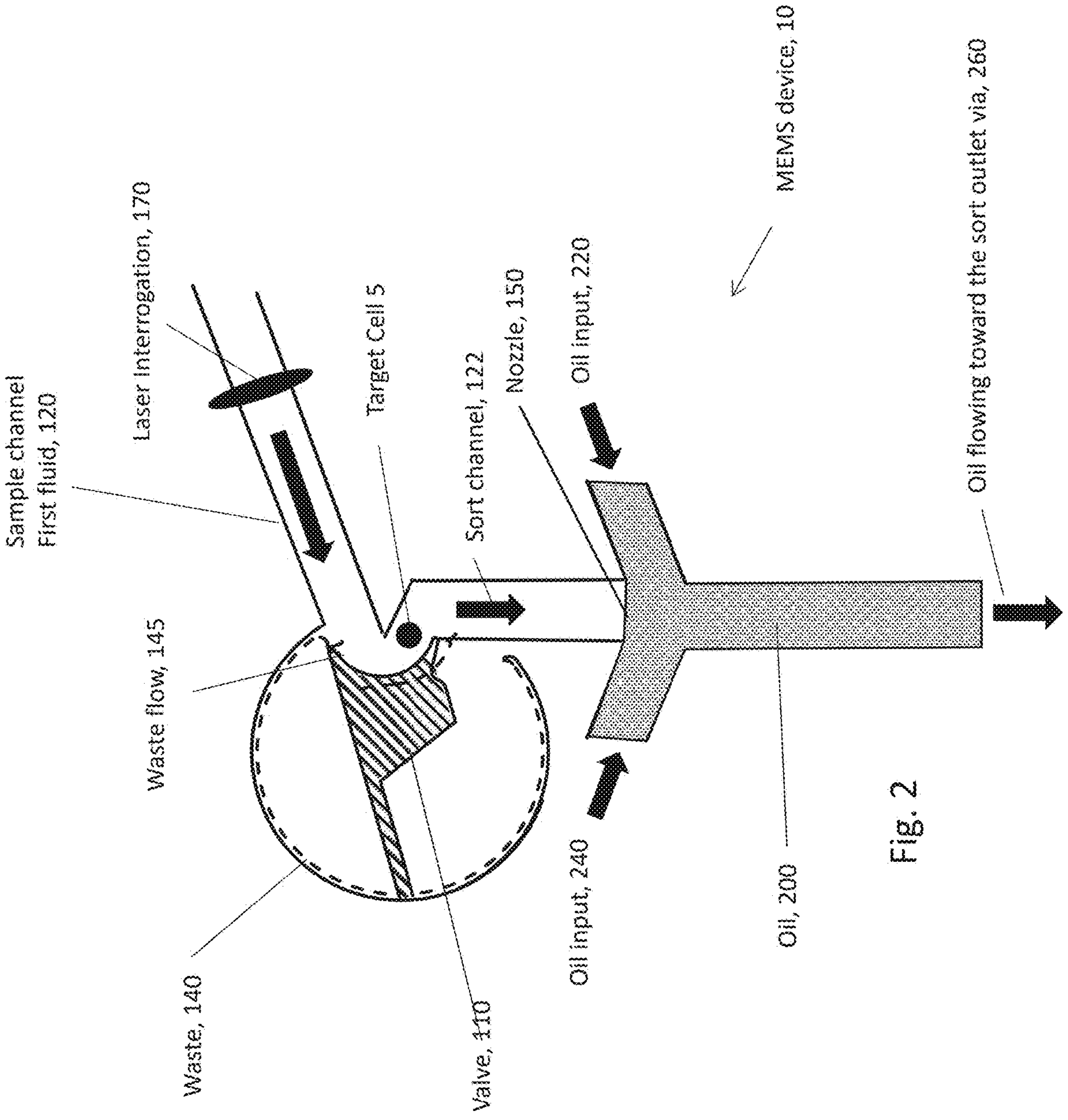
FIG. 2 is a schematic illustration of an embodiment of a microfabricated droplet dispenser with an immiscible fluid with the microfabricated MEMS fluidic valve in the open (sort) position.

The microfabricated MEMS valve may be, for example, the device shown generally in FIGS. 1 and 2. It should be understood that this design is exemplary only, and that other sorts of MEMS valves may be used in place of that depicted in FIGS. 1 and 2.

In the figures discussed below, similar reference numbers are intended to refer to similar structures, and the structures are illustrated at various levels of detail to give a clear view of the important features of this novel device. It should be understood that these drawings do not necessarily depict the structures to scale, and that directional designations such as “top,” “bottom,” “upper,” “lower,” “left” and “right” are arbitrary, as the device may be constructed and operated in any particular orientation. In particular, it should be understood that the designations “sort” and “waste” are interchangeable, as they only refer to different populations of particles, and which population is called the “target” or “sort” population is arbitrary.

FIG. 1 is an plan view illustration of the novel microfabricated fluidic MEMS droplet dispensing device 10 in the quiescent (un-actuated) position. The MEMS droplet dispensing device 10 may include a microfabricated fluidic valve or movable member 110 and a number of microfabricated fluidic channels 120, 122 and 140. The fluidic valve 110 and microfabricated fluidic channels 120, 122 and 140 may be formed in a suitable substrate, such as a silicon substrate, using MEMS lithographic fabrication techniques as described in greater detail below. The fabrication substrate may have a fabrication plane in which the device is formed and in which the movable member 110 moves. Details as to the fabrication of the valve 110 may be found in U.S. Pat. No. 9,372,144 (the '144 patent) issued Jun. 21, 2016 and incorporated by reference in its entirety.

A fluid sample stream may be introduced to the microfabricated fluidic valve 110 by a sample inlet channel 120. The sample stream may contain a mixture of particles, including at least one desired, target particle and a number of other undesired, nontarget materials. The particles may be suspended in a fluid, which is generally an aqueous fluid, such as saline. For the purposes of this discussion, this aqueous fluid may be the first fluid, and this first fluid may be immiscible in a second fluid, as described below.

The target particle may be a biological material such as a stem cell, a cancer cell, a zygote, a protein, a T-cell, a bacteria, a component of blood, a DNA fragment, for example, suspended in a buffer fluid such as saline. The fluid inlet channel 120 may be formed in the same fabrication plane as the valve 110, such that the flow of the fluid is substantially in that plane. The motion of the valve 110 may also be within this fabrication plane. The decision to sort/save or dispose/waste a given particle may be based on any number of distinguishing signals.

In one embodiment, the fluid sample stream may pass through an interrogation region 170, which may be a laser interrogation region, wherein an excitation laser excites fluorescent tag affixed to a target particle. The fluorescent tag may emit fluorescent radiation as a result of the excitation, and this radiation may be detected by a nearby detector, and thus a target particle or cell may be identified. Upon identification of the target particle or cell, the microfabricated MEMS valve may be actuated, as described below, and the flow directed from the nonsort (waste) channel 145 to the sort channel 122, as illustrated in FIG. 2. The actuation means may be electromagnetic, for example. The analysis of the fluorescent signal, the decision to sort or discard a particle, and the actuation of the valve, may be under the control of a microprocessor or computer.

In some embodiments, the actuation may occur by energizing an external electromagnetic coil and core in the vicinity of the valve 110. The valve 110 may include an inlaid magnetically permeable material, which is drawn into areas of changing magnetic flux density, wherein the flux is generated by the external electromagnetic coil and core. In other embodiments, other actuation mechanisms may be used, including electrostatic and piezoelectric. Additional details as to the construction and operation of such a valve may be found in the incorporated '144 patent.

In one exemplary embodiment, the decision is based on a fluorescence signal emitted by the particle, based on a fluorescent tag affixed to the particle and excited by an illuminating laser. Accordingly, these fluorescent tags may be identifiers or a barcoding system. However, other sorts of distinguishing signals may be anticipated, including scattered light or side scattered light which may be based on the morphology of a particle, or any number of mechanical, chemical, electric or magnetic effects that can identify a particle as being either a target particle, and thus sorted or saved, or an nontarget particle and thus rejected or otherwise disposed of.

This system may also be used to sort the labelled or barcoded bead. Accordingly, the "target particle" may be either a cell and/or a labelled bead.

With the valve 110 in the position shown in FIG. 1, the microfabricated MEMS fluidic valve 110 is shown in the closed position, wherein the fluid sample stream, target particles and non-target materials flow directly in to the waste channel 140. Accordingly, the input stream passes unimpeded to an output orifice and channel 140 which may be out of the plane of the inlet channel 120, and thus out of the fabrication plane of the device 10. That is, the flow is from the inlet channel 120 to the output orifice 140, from which it flows substantially vertically, and thus orthogonally to the inlet channel 120. This output orifice 140 leads to an out-of-plane channel that may be perpendicular to the plane of the paper showing FIG. 1. More generally, the output channel 140 is not parallel to the plane of the inlet channel 120 or sort channel 122, or the fabrication plane of the movable member 110.

The output orifice 140 may be a hole formed in the fabrication substrate, or in a covering substrate that is bonded to the fabrication substrate. Further, the valve 110 may have a curved diverting surface 112 which can redirect the flow of the input stream into a sort output stream, as described next with respect to FIG. 2. The contour of the orifice 140 may be such that it overlaps some, but not all, of the inlet channel 120 and sort channel 122. By having the contour 140 overlap the inlet channel, and with relieved areas described above, a route exists for the input stream to flow directly into the waste orifice 140 when the movable member or valve 110 is in the un-actuated waste position.

FIG. 2 is a schematic illustration of an embodiment of a microfabricated droplet dispenser with an immiscible fluid with the microfabricated MEMS device 10. In FIG. 2, the MEMS device 10 may include a MEMS fluidic valve 110 in the open (sort) position. In this open (sort) position, a target cell 5 as detected in the laser interrogation region 170 may be deflected into the sort channel 122, along with a quantity of the suspending (buffering) fluid.

In this position, the movable member or valve 110 is deflected upward into the position shown in FIG. 2. The diverting surface 112 is a sorting contour which redirects the flow of the inlet channel 120 into the sort output channel 122. The sort output channel 122 may lie in substantially the same plane as the inlet channel 120, such that the flow within the sort channel 122 is also in substantially the same plane as the flow within the inlet channel 120. Actuation of movable member 110 may arise from a force from force-generating apparatus (not shown). In some embodiments, force-generating apparatus may be an electromagnet, however, it should be understood that force-generating apparatus may also be electrostatic, piezoelectric, or some other means to exert a force on movable member 110, causing it to move from a first position (FIG. 1) to a second position (FIG. 2).

More generally, the micromechanical particle manipulation device shown in FIGS. 1 and 2 may be formed on a surface of a fabrication substrate, wherein the micromechanical particle manipulation device may include a microfabricated, movable member 110, wherein the movable member 110 moves from a first position to a second position in response to a force applied to the movable member, wherein the motion is substantially in a plane parallel to the surface, a fluid sample inlet channel 120 formed in the substrate and through which a fluid flows, the fluid including at least one target particle and non-target material, wherein the flow in the fluid sample inlet channel is substantially parallel to the surface, and a plurality of output channels 122, 140 into which the microfabricated member diverts the fluid, and wherein the flow in at least one of the output channels 140 is not parallel to the plane, and wherein at least one output channel 140 is located directly below at least a portion of the movable member 110 over at least a portion of its motion.

It should be understood that although channel 122 is referred to as the "sort channel" and orifice 140 is referred to as the "waste orifice", these terms can be interchanged such that the sort stream is directed into the waste orifice 140 and the waste stream is directed into channel 122, without any loss of generality. Similarly, the "inlet channel" 120 and "sort channel" 122 may be reversed. The terms used to designate the three channels are arbitrary, but the inlet stream may be diverted by the valve 110 into either of two separate directions, at least one of which does not lie in the same plane as the other two. The term "substantially" when used in reference to an angular direction, i.e. substantially tangent or substantially vertical, should be understood to mean within 15 degrees of the referenced direction. For example, "substantially orthogonal" to a line should be understood to mean from about 75 degrees to about 105 degrees from the line.

When the valve is in the open or sort position shown in FIG. 2, the suspending aqueous fluid, along with at least one suspended particle, may flow into the sort channel 122, and from there to the edge of the fabrication substrate. The fluid that was flowing in the fluid sample inlet channel 120 may then form a droplet at the edge of the fabrication substrate. Alternatively, the generated droplet might flow to and accumulate in the sort chamber.

Various structures may be used in this region to promote the formation of the droplet. These structures may be, for example, rounded corners or sharp edges which may influence or manipulate the strength or shape of the meniscus forces, wetting angle or surface tension of the first fluid droplet. These structures may be generally referred to as a "nozzle" indicating the region where the droplet is formed. At this nozzle point where the droplet is formed, an additional manifold may deliver an immiscible second fluid to the aqueous droplet, suspending the aqueous droplet in the fluid and preserving its general contours and boundary layers.

As mentioned, the valve 110 may be used to sort both a target cell and a bead. Laser induced fluorescence may be the distinguishing feature for either or both particles. These particles may both be delivered into a single droplet. These particles may be suspended in, and surrounded by, an aqueous first fluid, such as saline. Accordingly, the droplet may comprise primarily this first fluid, as well as the chosen particle(s), a target cell and/or a bead. The bead may be "barcoded", that is, it may carry identifying markers. The droplet may then be surrounded by an immiscible second fluid that is provided by a source of the second fluid, These features are described further below, with respect to a number of embodiments.

Accordingly, because of the flow in the microfabricated channels, droplets may be formed at the intersection with the immiscible fluid. These droplets may be encased in an immiscible second fluid, such as a lepidic fluid or oil 200, as shown in FIGS. 1 and 2. The oil 200 may be applied symmetrically by oil input 220 and oil input 240. The immiscible fluid may serve to maintain the separation between droplets, so that they do not coalesce, and each droplet generally contains only one target particle and only one bead. The stream of oil may exit the sort outlet via 260. The lipidic fluid may be a petroleum based lipidic fluid, or a vegetable based lipidic fluid, or an animal based lipidic fluid.

Figure 3:
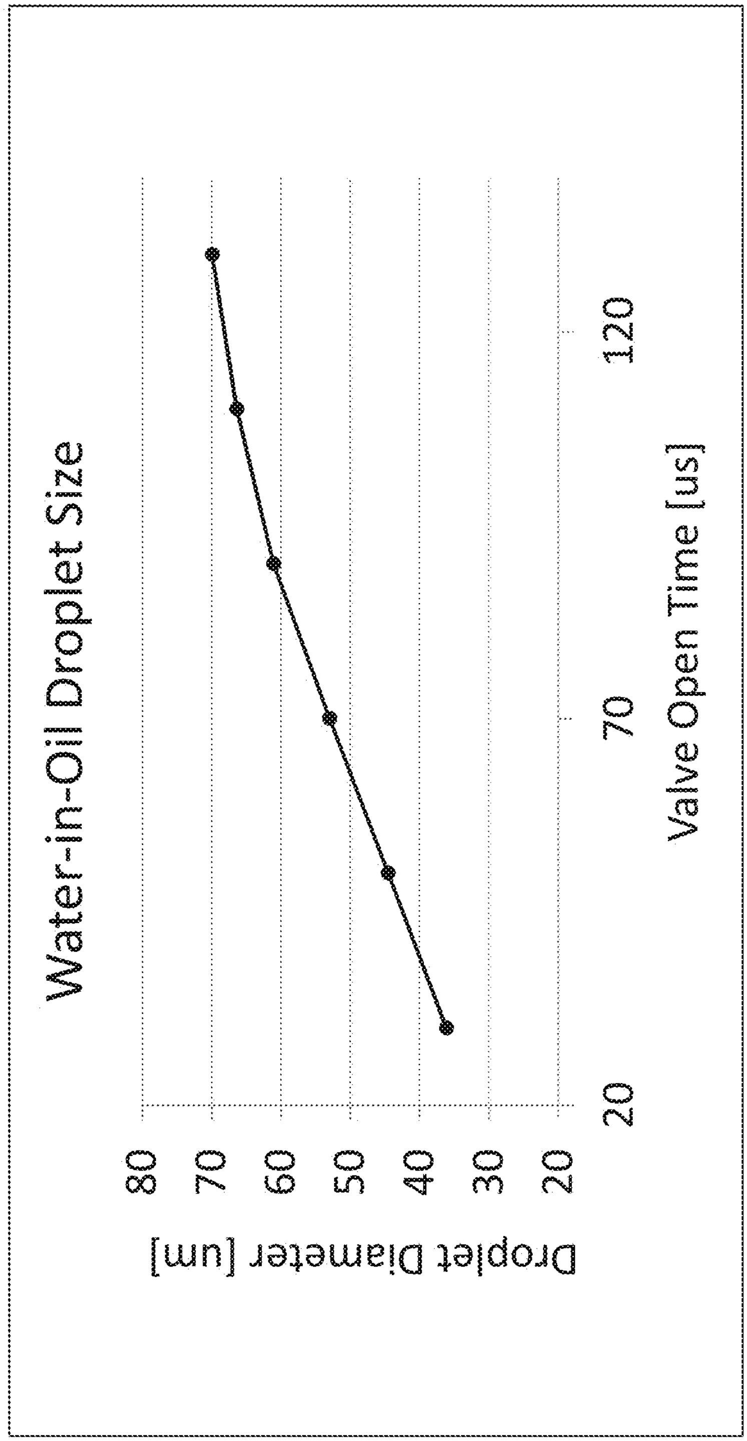
FIG. 3 is a chart showing the functional dependence of the water droplet size on the duration that the microfabricated MEMS fluidic valve is open.

The pace, quality and rate of droplet formation may be controlled primarily by the dynamics of the MEMS valve 110. That is, the quantity of fluid contained in the droplet, and thus the size of the droplet, may be a function of the amount of time that the MEMS valve 110 is in the open or sort position shown in FIG. 2. The functional dependence of the size of the droplet on the valve open time is illustrated in FIG. 3. As can be seen in FIG. 3, the diameter of the droplet is proportional to the valve open time, over a broad range of values. Only at exceedingly large droplets and long open times (greater than about 100 μsecs and 60 microns diameter) does the functional dependence vary from its linear behaviour.

Accordingly, the length of the sort pulse can determine the size of the generated droplet. If the pulse is too short, the oil meniscus may remain intact and no water droplet is formed. If the sort pulse is sufficiently long, a droplet may be formed at the exit and released into the stream of the second immiscible fluid.

If a target cell 5 is sorted within this time frame, the target cell 5 may be enclosed in the aqueous droplet. If the target particle is not sorted within this time frame, an empty aqueous droplet, that is, a droplet without an enclosed particle 5, may be formed. The situation is shown in FIG. 4.

As mentioned above, the MEMS valve 110 may be made on the fabrication surface of at least one semiconductor substrate. More generally, a multi-substrate stack may be used to fabricate the MEMS valve 110. As detailed in the '144 patent, the multilayer stack may include at least one semiconductor substrate, such as a silicon substrate, and a transparent glass substrate. The transparent substrate may be required to allow the excitation laser to be applied in the laser interrogation region 170.

The droplet 300 may be formed at the edge of the semiconductor substrate, or more particularly, at the edge of the multilayer stack. The droplet 300 may be formed at the exit of the sort channel 122 from this multilayer stack. In another embodiment, the droplet is not formed at the edge of the multilayer stack, but instead may be formed at the intersection of the sort flow and oil input, within the semiconductor substrate. At this location, a structure may be formed that promotes the formation of the droplet. This structure may include sharply rounded corners so as to manipulate surface tension forces, and the formation of meniscus and wetting angles. The structure designed to promote droplet formation may be referred to herein as a nozzle 150, and the term "nozzle" may refer generally to the location at which the droplet may be formed.

Figure 4:
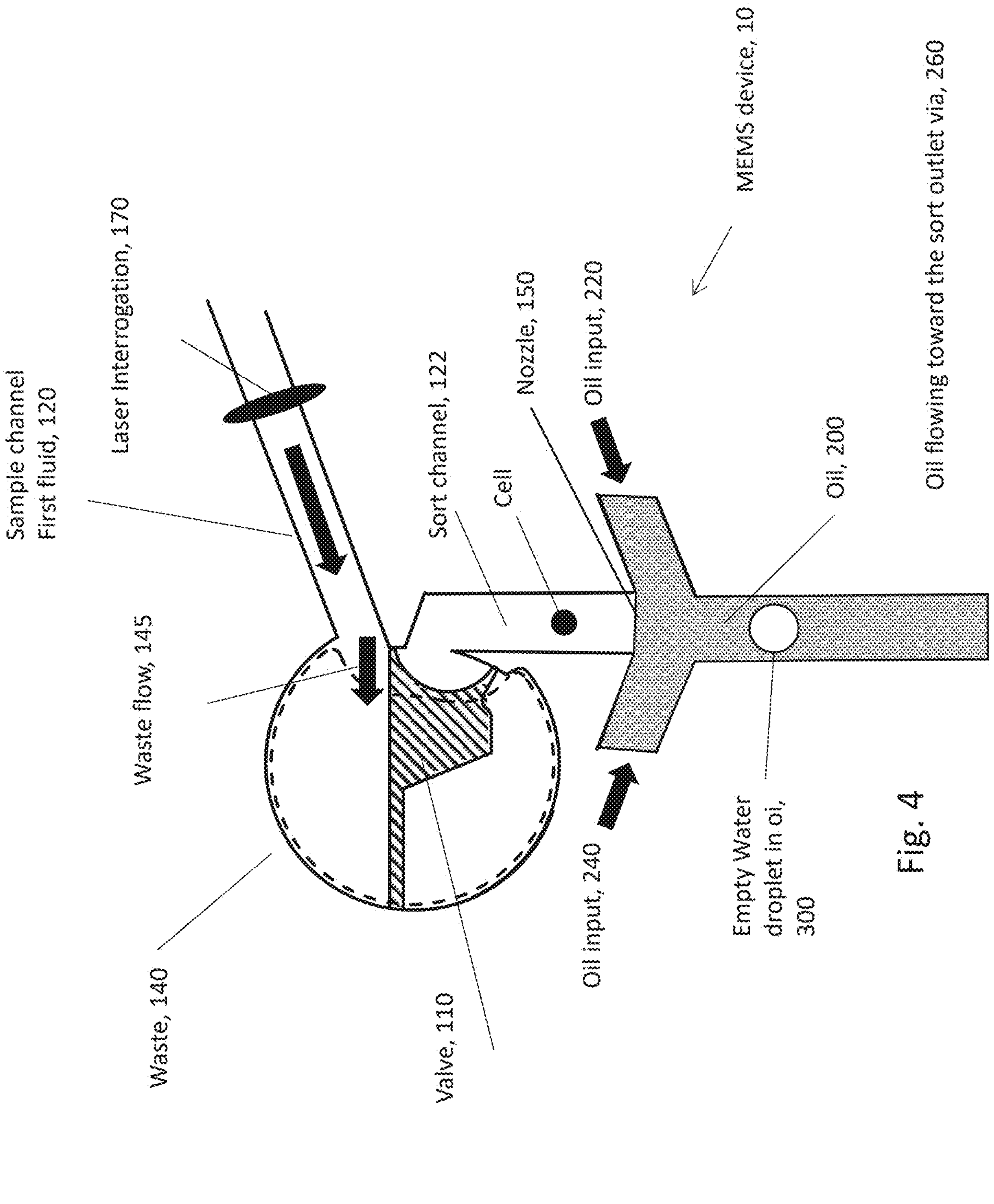
FIG. 4 is a schematic illustration of an embodiment of a microfabricated droplet dispenser with an immiscible fluid generating an empty droplet in oil.

In the structure shown in FIG. 4, downstream of the microfabricated MEMS valve, and in the vicinity of the nozzle structure 150, there may be disposed a flow junction with the immiscible second fluid. In the sort channel, downstream of the valve, there may be a flow junction with oil (as a carrier for water droplets) flowing from the sides towards the sort channel 122. This flow junction may have an inlet 220 and 240 on either end of the sort channel 122, forming an oil stream 200 downstream of the nozzle 150 and sort channel 122.

Sorting Strategy Using the Valve to Form a Droplet in Oil

The method for forming a droplet in oil may be as follows. A target cell is first detected in the laser interrogation region 170. A computer or controller may monitor the signals from the laser interrogation region. Upon detecting a target particle in the region, the computer or controller may send a signal to open the MEMS valve 110 by energizing the electromagnet. Magnetic interactions then move the MEMS valve as shown in FIG. 2. In this open (sort) position, a target cell 5 may be deflected into the sort channel, along with a quantity of the suspended fluid.

A bead is then sorted to accompany the sorted cell as a unique barcode. A second sort pulse is long enough to cause an instability in the oil-water interface and form a water droplet in oil containing the cell and the bead.

When the valve is stationary and no sorting occurs, as depicted in FIG. 1, oil continues flowing towards the sort outlet via, blocking water flow in the sort. In fact however, because of the finite gaps between the moving edges of the MEMS valve 110 shown in FIGS. 1 and 2, a small but finite amount of the fluid sample stream fluid may continue to flow down the sort channel 122. However, these leak flow rates through the valve gaps, are not sufficient to break the oil front and create a water droplet, in normal operation.

However, as oil may continue to flow, the effluent may be directed into a waste receptacle, until a target particle is detected. It may also be the case that continued leakage of the fluid sample stream through the gaps around the MEMS valve 110, may eventually cause a water droplet to form. Because no target cell has been detected, and the MEMS valve 110 has not been opened, this aqueous droplet may be empty.

Accordingly, FIG. 4 is a schematic illustration of an embodiment of a microfabricated droplet dispenser with an immiscible fluid generating an empty first fluid droplet 300 in oil 200. This situation may occur if no target particle is present in the fluid sample stream. The MEMS valve 110 may leak slightly, causing an aqueous droplet to form but without an enclosed target particle. In this case, the droplet may be allowed to flow into a waste area of a holding receptacle.

Figure 5:
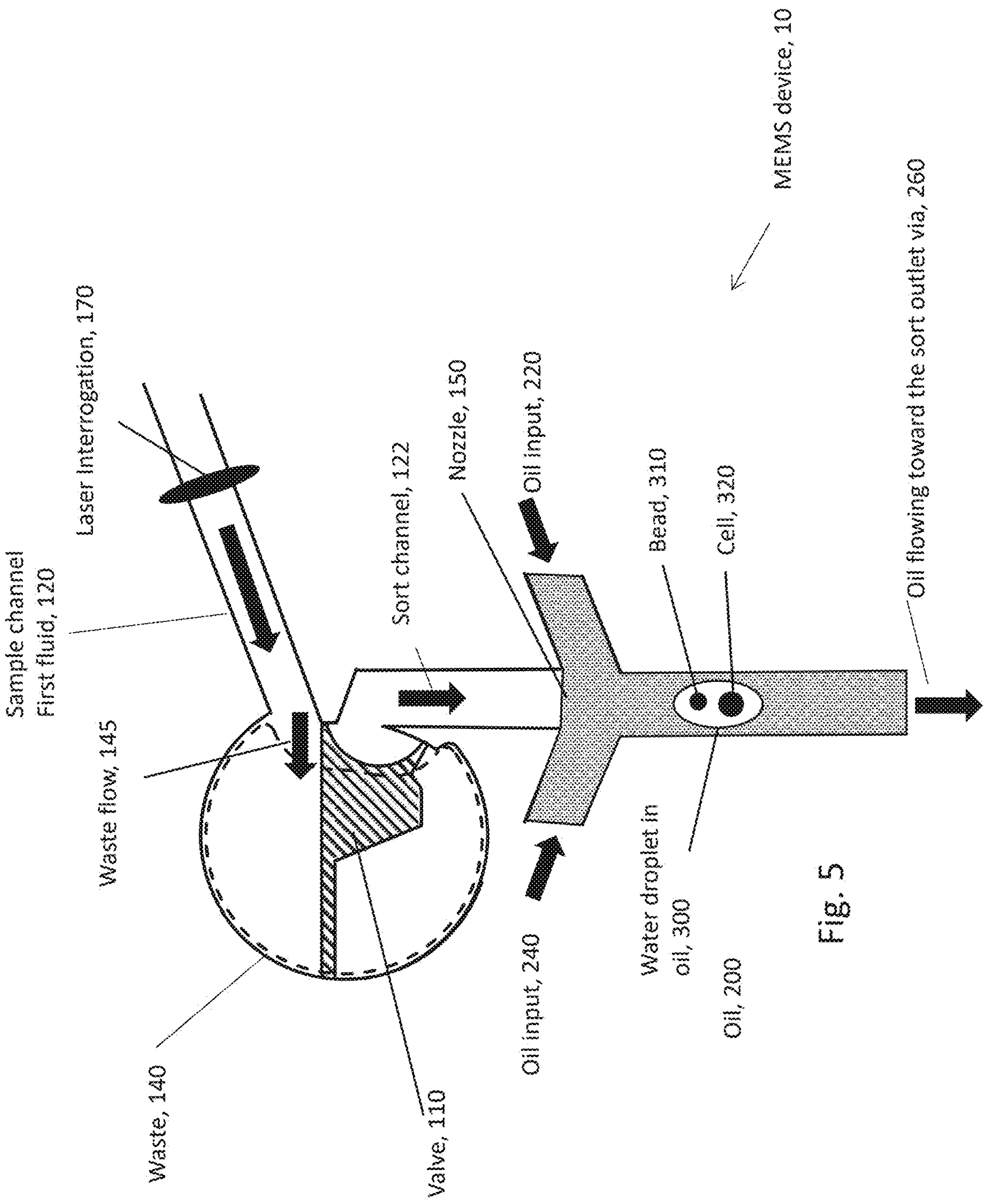
FIG. 5 is a schematic illustration of an embodiment of a microfabricated droplet dispenser with an immiscible fluid generating a droplet, wherein the droplet contains both a particle and a bead.

In another embodiment, the MEMS valve 110 may sort both a target particle 5 (here, a target cell 320) and a bead 310, as shown in FIG. 5. The bead may be a biologically inert material coated with a biologically active material, and additional compounds. The biologically active materials may be antibodies that can become conjugated to antigens appearing on a target cell surface 320. In addition to the antigens and inert materials, the bead may further be coupled to a plurality of fluorescent tags, that is, compound which fluoresces when irradiated by an excitation laser of the proper wavelength and intensity. This plurality of fluorescent tags may be different for each bead 310, and may therefore act as a signature or identifier for the bead.

When a bead 310 is in proximity to a target cell 320, and the antibodies of the bead 310 may become conjugated with the antigens of the cell, the bead, along with its identifying fluorescent tags, may become affixed to the cell 320. Thus, the bead 310 provides an identifying marker for the cell 320, or a "barcode" which identifies the cell. A computer or controller may associate this particular barcode with the particular cell. Accordingly, a large number of such droplets may be placed in a small volume of fluid, each containing a target cell and identifying barcode and all within a field of view of a single detector. This may allow a very large number of biological assays or polymerase chain reactions, to be undertaken in parallel, and under a single detection system.

FIG. 5 is a schematic illustration of an embodiment of a microfabricated droplet dispenser with an immiscible fluid generating a droplet in oil, wherein the droplet contains both a particle or cell 320 and a bead 310. Accordingly, the MEMS valve 110 may first sort a particle 320, enclosing the particle 320 in an aqueous droplet as described above. The MEMS valve 110 may then also sort a barcoded bead 310, and both particle 320 and the bead 310 may be enclosed in the same aqueous droplet, as shown in FIG. 5.

Figure 6:
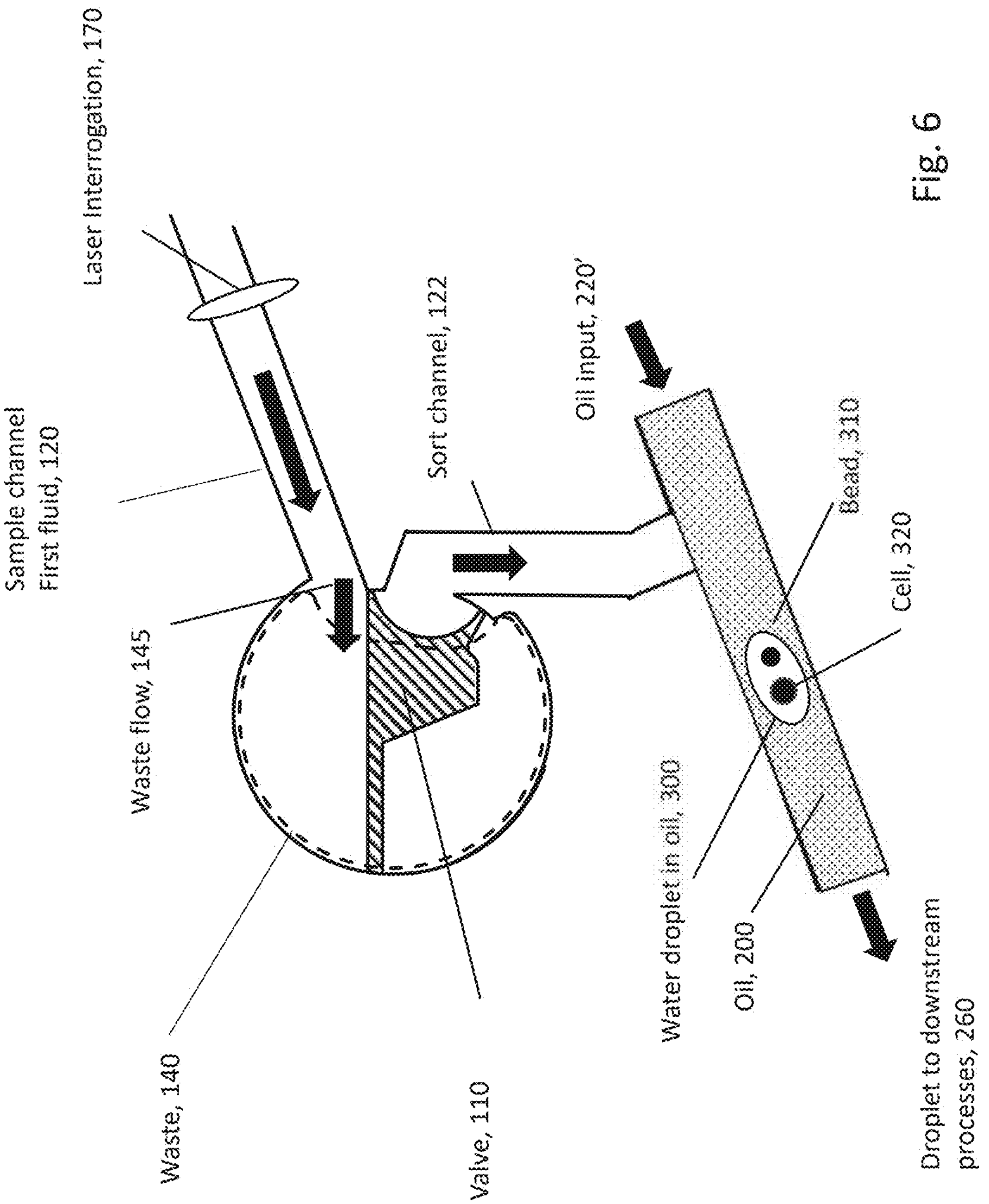
FIG. 6 is a schematic illustration of an embodiment of a microfabricated droplet dispenser with an immiscible fluid in a butt junction.

FIG. 6 is a schematic illustration of another embodiment of a microfabricated droplet dispenser with an immiscible fluid in a butt junction. In this embodiment, the application of the surrounding second immiscible fluid is asymmetrical. Instead of coming both from the right and the left of the nozzle region, the oil 200, the oil junction is applied in parallel to the sort channel 122 and may exit downstream 260 of the sort channel 122. The second immiscible fluid may flow from right to left. The aqueous fluid droplet may break the oil meniscus from the side channel, as shown. As before, each droplet 300 in oil 200 may contain both a target cell 320 and an identifying bead 310.

Laser Assisted Droplet Formation

Figure 7:
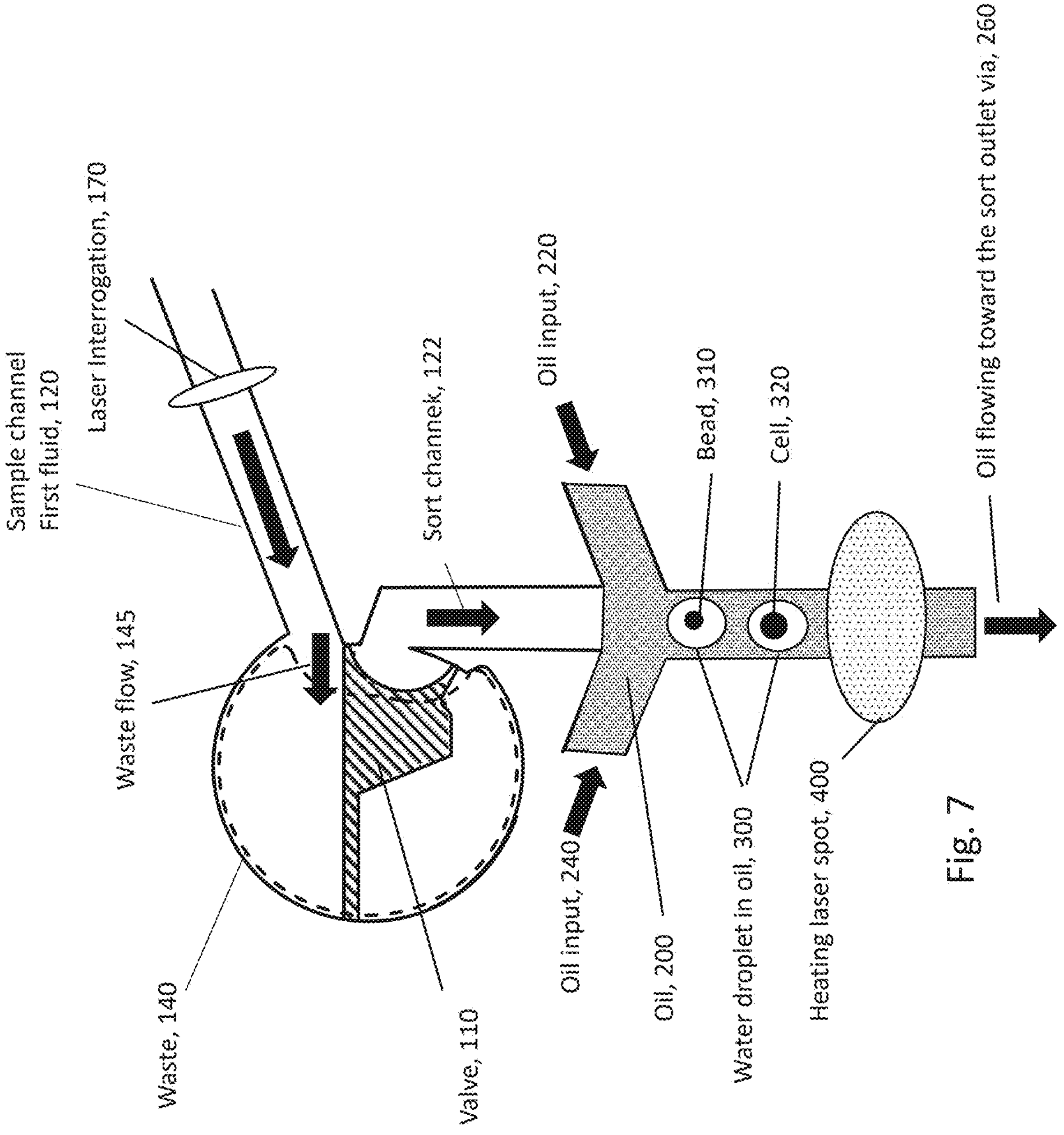
FIG. 7 is a schematic illustration of an embodiment of a microfabricated droplet dispenser with a laser assisted droplet coalescence.

FIG. 7 is a schematic illustration of another embodiment of a microfabricated droplet dispenser with a laser assisted droplet coalescence. In this embodiment, the two particles the target cell 320 and the bead 310 are sorted separately and placed into two separate aqueous droplets in the oil stream 200. For each event, the passage of the target cell 320 and the passage of the bead 310, the sort pulse is long enough to cause an instability in the oil-water interface and form a water droplet in oil containing the cell. The two separate droplets are then merged by application of laser light 400 on to oil channel containing the aqueous droplets.

Any of a variety of pulsed or continuous wave lasers may be suitable for this application. For example, a pulsed $CO_2$ laser may be directed onto the channel as shown in FIG. 7, to heat the droplets. The application of energy causes the fluids to heat, which weakens meniscus and membrane forces, allowing the droplets to merge.

In FIG. 7, as in previous embodiments, the microfabricated droplet dispenser in FIG. 7 may have a symmetric (or asymmetric) oil input configuration. In either configuration, the droplets 300 may be encased in an immiscible second fluid, such as a lepidic fluid or oil 200. The oil 200 may be applied symmetrically by oil input 220 and oil input 240. The stream of oil may exit the sort outlet via 260.

The embodiment shown in FIG. 7 may have a flow channel which is capable of sorting two aqueous droplets, and then merging them into a single larger droplet. In this embodiment, the sort pulse is long enough to cause an instability in the oil-water interface and form a water droplet in oil containing the cell. Then a bead is sorted and a separate droplet is formed. Accordingly, the first droplet may contain a target cell 320, and the second aqueous droplet may contain a bead 310 as previously described. A merging area is a portion of the sort flow channel 122 wherein the laser 400 is directed. The laser light may be focused to increase its peak intensity. The applied laser light may heat the droplet as well as the surrounding fluid, and allow the two droplets to merge. The merging may be caused by the laser-induced heating and consequent weakening of surface tension of the fluid droplet.

Alternatively, the first droplet may contain the bead 310, and the second aqueous droplet may contain the target cell 320. In either case, the application of heat onto the channel in the laser 400 may serve to heat the fluids and allow the two droplets to merge. Accordingly, at the output of the microfabricated droplet dispenser may emerge an aqueous droplet encased in oil wherein the droplet contains both a target cell 320 and a bead 310. The bead 310 may have a fluorescent barcode affixed to it, and the bead may be conjugated to the target cell 320.

Geometry-Induced Flow Slowdown

Figure 8:
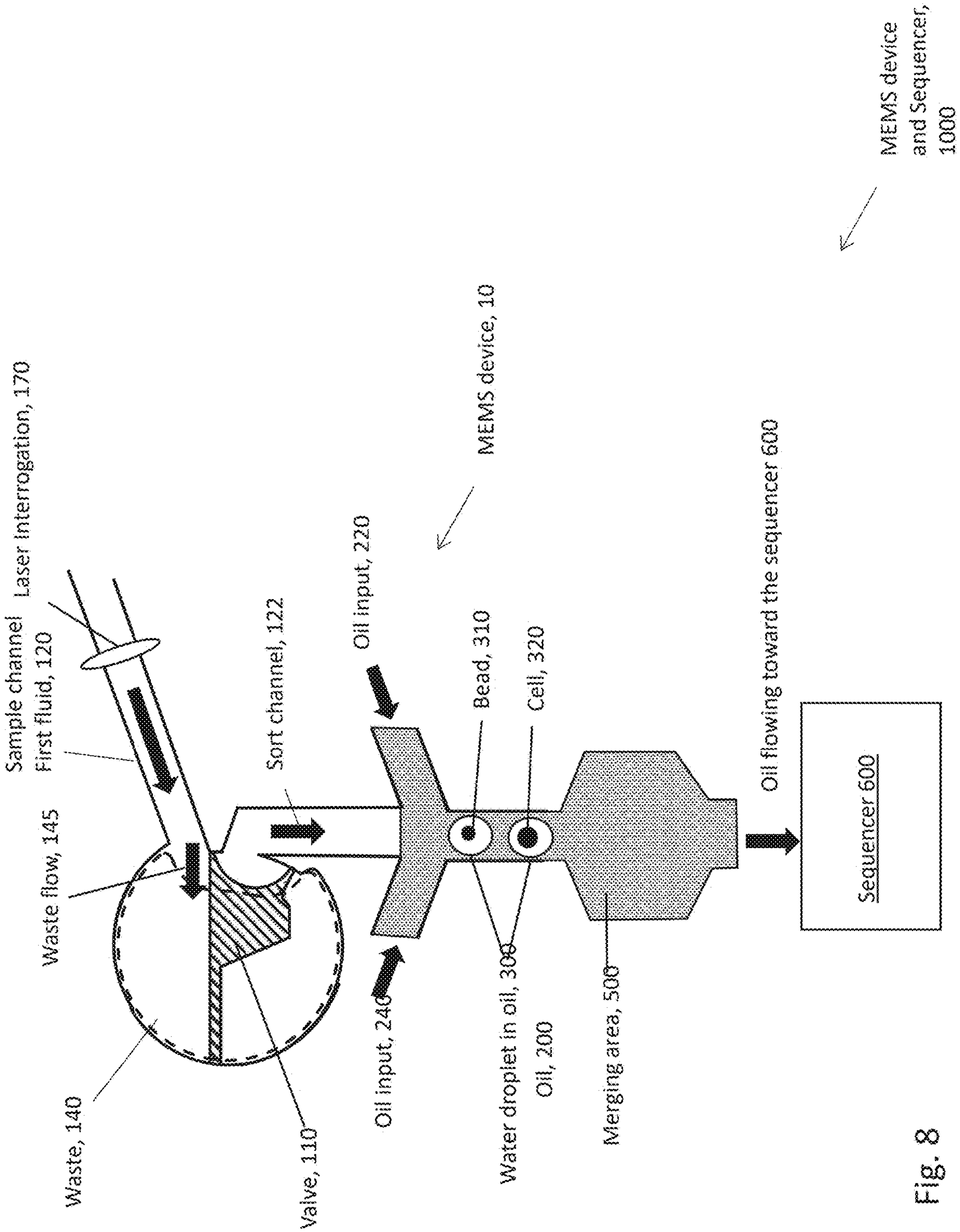
FIG. 8 is a schematic illustration of an embodiment of a microfabricated droplet dispenser with a variable channel cross section, coupled to a genetic sequencer.

FIG. 8 is a schematic illustration of an embodiment of a microfabricated droplet dispenser with a variable channel cross section. Like previous embodiments, the microfabricated droplet dispenser in FIG. 8 may have a symmetric (or asymmetric) oil input configuration. In this configuration, the droplets may be encased in an immiscible second fluid, such as a lepidic fluid or oil 200. The oil 200 may be applied symmetrically by oil input 220 and oil input 240. The stream of oil may exit the sort outlet via 260.

The embodiment shown in FIG. 8 may have a flow channel which is capable of sorting two aqueous droplets, and then merging them into a single larger droplet. In this embodiment, the sort pulse is long enough to cause an instability in the oil-water interface and form a water droplet 300 in oil containing the cell. Then a bead 310 is sorted and a separate droplet is formed. Accordingly, the first droplet may contain a target cell 320, and the second aqueous droplet may contain a bead 310 as previously described. A merging area 500 is a portion of the sort channel 122 having a variable cross section 500. The sudden widening of the channel in the merging area 500 may serve to slow the flow down within the merging area, allowing the two droplets to merge. In other words, the sudden widening may produce geometry-induced flow slowdown, which allows the droplets to merge.

Alternatively, the first droplet may contain the bead 310, and the second aqueous droplet may contain the target cell 320. In either case, the sudden widening of the channel in the merging area 500 may serve to slow the flow down within the merging area, allowing the two droplets to merge. Accordingly, at the output of the microfabricated droplet dispenser may emerge an aqueous droplet 300 encased in oil 200 wherein the droplet 300 contains a target cell 320 and a bead 310. The bead 310 may have a fluorescent barcode affixed to it, and the bead may be conjugated to the target cell 320.

Accordingly, described here is a microfabricated droplet dispenser, comprising a microfluidic channel formed in a substrate and a fluid flowing in the microfluidic fluid channel; a microfabricated MEMS fluidic valve, configured to open and close the microfluidic channel, a droplet comprising a first fluid dispensed at an end of the microfluidic channel, wherein a dimension of the droplet is determined by a timing of opening and closing of the microfabricated microfluidic valve, and a source of a second fluid immiscible with the first fluid wherein the droplet is dispensed from the microfluidic channel into, and immersed in, the second immiscible fluid.

The droplet dispenser may further comprise a fluid sample stream flowing in the microfluidic channel, wherein the fluid sample stream comprises target particles and non-target material, an interrogation region in the microfluidic channel, wherein a target particle is identified among non-target material; and wherein the microfabricated MEMS fluidic valve is configured to separate the target particle from the non-target material in response to a signal from the interrogation region, and direct the target particle into the droplet. It may also include a bead attached to a plurality of fluorescent tags, wherein the fluorescent tags specify the identity of the bead with a fluorescent signal, and wherein the microfabricated MEMS fluidic valve is configured to separate the bead and direct the bead into the droplet, wherein the bead and a target particle, are located within the same droplet. The bead may comprise a plurality of fluorescent tags, such that the bead has an identifying fluorescent signature. The bead may also have at least one antibody, that binds to an antigen on the target particle.

The microfabricated MEMS valve may move in a single plane when opening and closing, and wherein that plane is parallel to a surface of the substrate. The droplet may be dispensed at a nozzle structure formed in the microfluidic channel in the substrate. The source of immiscible fluid is disposed symmetrically about the nozzle. Surfactant may be added to the fluid stream.

The droplet dispenser may further comprise a laser focused on the microfluidic channel upstream of the nozzle, heating the droplet to assist in severing the droplet from the fluid in the microfluidic channel, or to heat the droplet to coalesce adjacent droplets in the microfluidic channel. The microfluidic channel may have a channel widened area, wherein the cross section of the channel increases and then decreases. The microchannel may intersect the source of immiscible fluid in a butt junction. The target particles are at least one of T-cells, stem cells, cancer cells, tumor cells, proteins and DNA strands.

A method for dispensing droplets is also described. The method may include method may include forming a microfluidic channel on a substrate, providing a fluid flowing in the microfluidic fluid channel, opening and closing a microfabricated MEMS fluidic valve, The method may further comprise opening and closing a microfabricated MEMS fluidic valve, to open and close the microfluidic channel, capturing at least one of a target particle and a bead with identifiers disposed thereon, providing a source of an immiscible second fluid, immiscible with the first fluid, and dispensing a droplet of the first, wherein a dimension of the droplet is determined by a timing of opening and closing of the microfabricated microfluidic valve, and wherein the droplet encloses at least one of the bead and the target particle.

The fluid flowing in the microfluidic channel may include target particles and non-target material. The method may further include identifying a target particle among non-target material in a laser interrogation region, opening and closing the microfabricated MEMS fluidic valve to separate the identified target particle from the non-target material in response to a signal from the interrogation region, and directing the target particle into the droplet.

The method may also include providing a bead attached to a plurality of fluorescent tags, wherein the fluorescent tags specify the identity of the bead with a fluorescent signal, separating the bead using the microfabricated MEMS fluidic valve, and directing the bead into the droplet, wherein the bead and the target particle, are located within the same droplet.

The droplet may be formed at a nozzle structure formed in the substrate. The method may further include heating the fluid with a laser focused just upstream of the nozzle.

The droplets formed by the system. MEMS device 10, described above may be coupled to a genetic sequencer or simply referred as sequencer 600, or other cellular or genetic manipulation, and thereby obtain detailed information relating to a singular, specific biological particle or cell. The MEMS device 10 may be uniquely suited to the sequencing application because the fluid transport of the droplet containing the biological particle is enclosed throughout, and the forces used to guide the droplet and particle are gentle. This allows improved sterility and viability of the biological material. Accordingly, the MEMS device 100 may be coupled to a genetic sequencing apparatus, thus delivering a well characterized genetic sample in a droplet contained in an immiscible fluid stream.

The system 1000 is shown in FIG. 8, with the sequencer 600 coupled to the MEMS device 10, to create the MEMS device and sequencer 1000. In addition, an identifying label or barcode may be affixed to the particle, such that the genomic sequence is associated with a single, identified, particular biological particle.

This whole single cell sequencer 1000 may operate generally as follows:

1) Put ONE cell and chemistry including the barcode information into ONE droplet
2) Lyse cell to set DNA and RNA free
3) Fragment the DNA/RNA, optionally followed by some further chemistry. Label fragments of DNA/RNA with barcode information
4) Sequence fragments and via barcode to find out what specific cell had what genetic information. Sequencing may make use of a genetic library, depending on the sequencing technique. These steps and techniques are described in further detail with respect to the embodiment discussed below. The details of these steps can also be found in the following documents, all of which are incorporated by reference in their entireties.

1) "Methods and Systems for Associating Physical and Genetic Properties of Biological Particles" PCT/US2018/061629, 16 Nov. 2018 (WO2020207963)
2) "Conjugates Having An Enzymatically Releasable Detection Moiety And a Barcode Moiety" (PCT/EP2020/059747, filed Apr. 6, 2020 (WO 2019099908)
3) "COLOR AND BARDCODED BEADS FOR SINGLE CELL INDEXING" 12 Nov. 2020, PCT/EP2020/081851
4) EP20182775.5 "METHOD COMBINING SINGLE CELL GENE EXPRESSION MAPPING AND TARGETED RNA OR c-DNA SEQUENCING USING PADLOCK OLIGONUCLEOTIDES COMPRISING A BARCODE REGION" Jun. 29 2020, EP20182775.5

What follows is an embodiment of the system and method outlined generally above. In the following description, certain terms of art may be used. While these terms are widely known to those skilled in the art, to avoid confusion the following definitions are offered:

cDNA is complementary DNA, which is DNA synthesized from a single-stranded RNA (e.g., messenger RNA (mRNA) or microRNA (miRNA)) template in a reaction catalyzed by the enzyme reverse transcriptase.

Barcoded primers are single ended oligonucleotides that contain predefined sequences. These sequences can later on be decoded again and can be used as a unique identifier for each detected cell in the process. In the present application barcoded primers contain oligo(dT) which will interact with the poly A tail of the mRNA, a unique barcode and molecular identifier (UMI).

RT reagents are all reagents used to do reverse transcription of RNA to cDNA. Usually RT reagents contain an enzyme such as reverse transcriptase, random hexamers, oligo (dT) and sequence specific reverse primers.

Reaction vesicles are the reactors where the reaction takes place. In this application reaction vesicles are the water in oil droplet with the bead and cell.

NGS stands for next generation sequencing and allows the determination of sequences in a massively parallel manner.

RCA stands for rolling circle amplification. It is a method of isothermal amplification of circular DNA molecules.

Rolonies are the product of the RCA process.

Poly A-tailed means the polyadenylation of a RNA transcript. Poly A-tail sequences only contain adenine bases.

Adaptor oligos are used during library preparation for sequencing. Adapter oligos allow to fish out short target DNA sequences of interest.

SPRI beads stands for solid phase reversible immobilization beads. Those beads are usually magnetic with a carboxyl group coating and are able to bind DNA. SPRI beads can therefore be used to do size selection.

Figure 9:
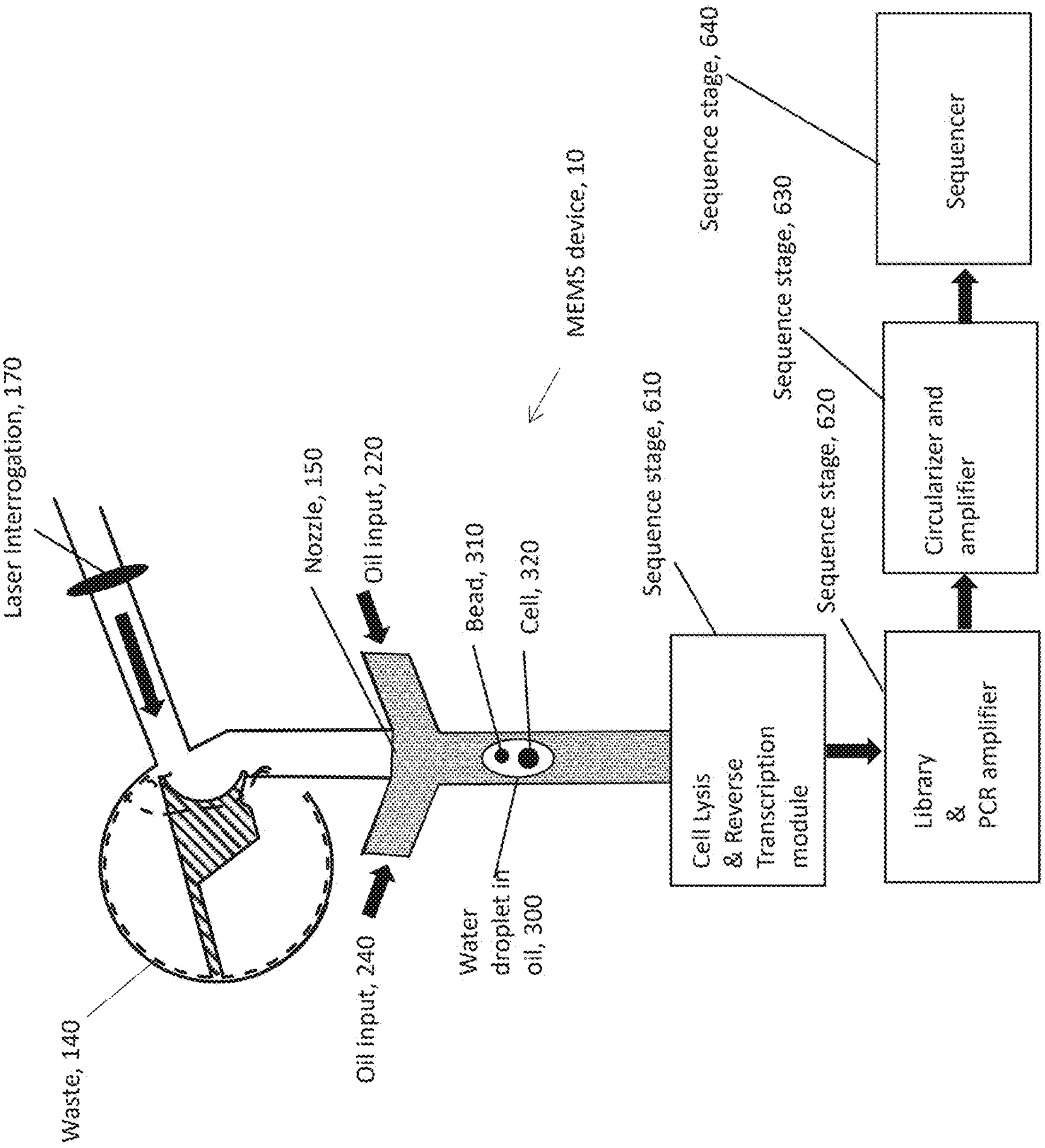
FIG. 9 illustrates components of the sequencer in further detail.

In FIG. 9, the sequencer is further depicted as including a number of modules 310-340. It should be understood that not all of these modules may be necessary to practice this invention, but that FIG. 9 is merely illustrative of a sequencing embodiment. First, each droplet may further encapsulate a barcoded bead 310.

Each bead encapsulated in the droplets contains many barcoded primers. The beads provides primers that contain oligo(dT) which will interact with the poly A tail of the mRNA, a unique barcode and molecular identifier (UMI) that are used to index the 3' end of cDNA molecules during reverse transcription, thus enabling the assignment of every individual transcripts and individual cells and finally the primers provide by the beads contain a PCR handle for further amplification of the library construct.

The Sequencer 600 may further include a Cell lysis & RT stage 610. Each functional water droplet in oil contains a single cell, a single bead with primers as described in 310, and RT reagents. Within each reaction vesicle, a single cell is lysed and reverse transcription of polyadenylated mRNA occurs. As a result, all cDNAs from a single cell will have the same barcode, allowing the sequencing reads to be mapped back to their original single cells of origin. After that step the droplets are pooled together and a alcohol based reagent is added to dissolve the oil water droplet solution. A washing step is introduced to get rid of unwanted leftovers. The preparation of NGS libraries from these barcoded cDNAs is then carried out in a highly efficient bulk reaction.

The Sequencer 600 may further include a library preparation stage, 620: The barcoded double stranded cDNA are used to prepare an NGS library using conventional and prior art approach. The cDNA is fragmented enzymatically and post fragmentation, the ends are repaired and poly A-tailed. Adaptor oligos are then ligated to each extremity clean up with SPRI beads and amplified by PCR.

The Sequencer 600 may further include a Circularization and amplification, stage 630: The cDNA library containing adaptors is then used as a template for rolling circle amplification (RCA). The RCA reaction needs to be primed using an oligonucleotide (RCA primers) that is complementary to the common adapter portion of the circularized DNA library. This short duplex/circular template is recognized by the Polymerase performing the RCA which amplifies the DNA regardless of the target sequence into DNA rolonies containing several hundred copies or concatemers of the DNA.

The Sequencer 600 may further include a Sequencing stage, 640: The rolonies are then loaded in to a micro fluidics channel. The rolonies will randomly immobilize on a functionalized glass surface. Multiple different chemistry reagents are sequentially applied to sequence the bases on each rolony. The bases are labeled with fluorescence dyes which an optical imaging system can detect during each cycle of sequencing. A sophisticated algorithm takes all those raw images coming from the optical imaging system and does the base calling for each rolony and determines the bases.

Figure 10:
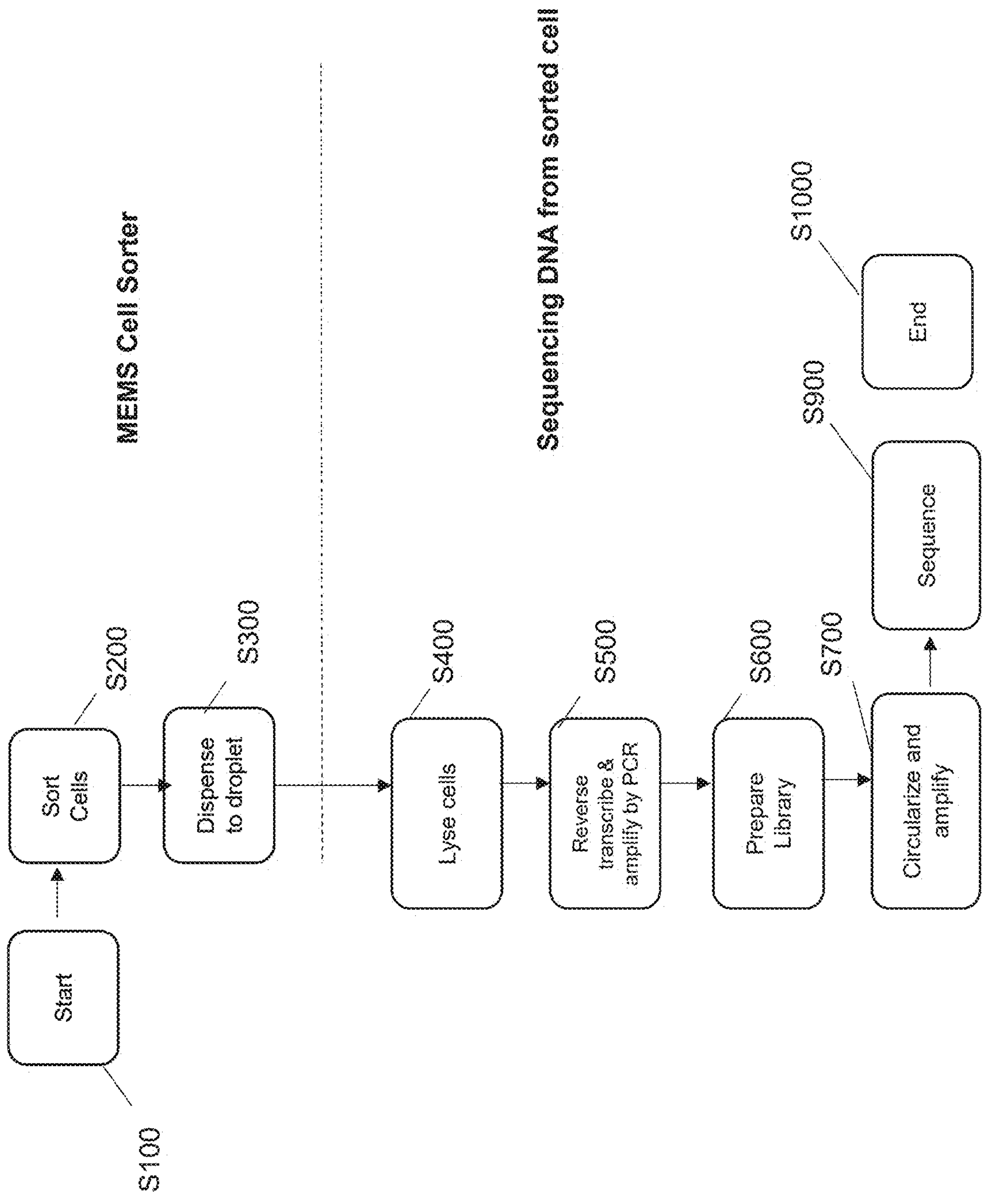
FIG. 10 illustrates a method for sequencing the genetic material contained in the droplet.

A process or method to sequence the genetic material of a single biological particle separated from the fluid stream by the MEMS device 10 is also disclosed here, and this method is illustrated in FIG. 10. The method may begin in step S100. In step S200 the cells are sorted. In step S300, the cells are dispensed into a droplet and the droplet is inserted into a flowing stream of an immiscible fluid. Is step S400, the droplet is destroyed, and the cell is lysed to release the genetic material encapsulated therein. In step S500, the genetic material is reverse transcribed and amplified by polymerase chain reaction. In step S600 the cDNA libaray is prepared. In step S700, the genetic material is circularized and amplified in an RCA. In step S900, the sequence is ascertained by successive application of a fluorescent reagent, and imaging of the sample.

It should be understand that not all of these step need necessarily be performed, and they may not need to be performed in the precise order given in FIG. 11. Furthermore, each of these steps may include a number of sub-steps. For example, in step S900 "sequence", the sample of genetic material may first be introduced into a microchannel and then immobilized on a functionalized glass surface.

Accordingly, disclosed here is a microfabricated droplet dispenser. The droplet dispenser may include a microfluidic channel formed in a substrate, a first fluid, including at least one target particle and at least one bead and non-target material, a microfabricated MEMS fluidic valve, configured to open and close the microfluidic channel and formed in the same substrate wherein the MEMS valve when in the sort position, separates the target particle and redirects the target particle into a first sort channel containing the first fluid, a second fluid, immiscible with the first fluid. The second fluid may be contained in a second microfluidic channel containing the second immiscible fluid, a nozzle disposed between the first sort channel and the second microfluidic channel, wherein the nozzle forms a droplet comprising a quantity of the first fluid along with the target particle, the quantity determined by the MEMS fluidic valve opening and closing, a fluidic manifold that accepts the droplet and lyses the target particle enclosed within the particle to release genomic material; and a sequencer that sequences the genomic material.

The system may further comprise a magnetic bead attached to a barcode, wherein the barcode uses single ended oligonucleotides that are containing predefined sequences, wherein the microfabricated MEMS fluidic valve also separates the magnetic bead and delivers it into the same droplet as the target particle, such that the droplet contains the aqueous fluid, the target particle and the barcoded bead, and flows in a stream of the immiscible second fluid.

The sequencer may be an NGS sequencer, and may further comprises a cell lysis and transcription module, and wherein the NGS sequencer sequences at least one of the genomic material and the barcode. The sequencer may also include a cDNA library and a polymerase chain reaction amplification stage. The cDNA may comprises adaptors used as a template for rolling circle amplification (RCA). The RCA stage may produce rolonies.

The sequencer may further comprises a library preparation stage which prepares a genomic library, and sequences a region of interest from the genomic material using the genomic library. The sequencer may further comprise a sequencing stage which detects the amino acid sequence of the genomic material by successive application of chemistry reagents and imaging. The sequencer may further comprise a second microfluidic channel having a functionalized surface, wherein the rolonies adhere to the functionalized surface.

The system may further comprise an interrogation region in the microfluidic channel; and a laser directed into the laser interrogation region, wherein the laser identifies target particles, and wherein the microfabricated MEMS fluidic valve is configured to separate the target particles from the non-target material in response to a signal from the interrogation region, and direct the target particle into the droplet.

The system may further comprise a bead disposed in the first fluid, wherein the bead is attached to a plurality of fluorescent tags, wherein the fluorescent tags identify the bead with a fluorescent signal, and wherein the microfabricated MEMS fluidic valve is configured to separate the bead and direct the bead into the droplet, wherein the bead and a target particle, are both located within the same droplet. The bead may be coupled to the target particle. The microfabricated MEMS fluidic valve, may move in a single plane when opening and closing, and wherein that plane is parallel to a surface of the substrate.

Also disclosed her is a process for separating and analyzing genomic material. The process may include forming a first fluidic channel on a substrate, providing a first fluid flowing in the first microfluidic fluid channel, opening and closing a microfabricated MEMS fluidic valve, to open and close the microfluidic channel, capturing at least one of a target particle and a bead with identifiers disposed thereon. The process may further include providing a source of an immiscible second fluid, immiscible with the first fluid, wherein the immiscible second fluid flows in a second fluidic channel, forming a nozzle at the output of the first fluidic channel which dispenses a droplet into the second fluidic channel, dispensing the droplet of the first fluid into the immiscible second fluid, wherein a dimension of the droplet is determined by a timing of opening and closing of the microfabricated microfluidic valve, and wherein the droplet encloses at least one of the bead and the target particle having a genomic sequence, and wherein both the droplet with the quantity of the first fluid and the second immiscible fluid flow within the microfluidic microchannel formed in the substrate; and sequencing the genomic material.

The sequencing of the genomic material may further comprises lysing the target particle to release the genomic material.

The method may further comprise providing a bead attached to a plurality of fluorescent tags, wherein the fluorescent tags specify the identity of the bead with a fluorescent signal, separating the bead using the microfabricated MEMS fluidic valve; and directing the bead into the droplet, wherein the bead and the target particle, are located within the same droplet.

The sequencing may further comprise using the cDNA library as a template for rolling circle amplification (RCA). The RCA may be primed using an oligonucleotide (RCA primers) that is complementary to the common adapter portion of the circularized DNA library. The template may be recognized by the polymerase performing the RCA which amplifies the DNA regardless of the target sequence into DNA rolonies containing several hundred copies or concatemers of the DNA. The method may further comprise loading the rolonies into a microfluidic channel, immobilizing the rolonies on a functionalized glass surface, and sequentially applying reagents to discern the sequence of the genomic material.

While various details have been described in conjunction with the exemplary implementations outlined above, various alternatives, modifications, variations, improvements, and/or substantial equivalents, whether known or that are or may be presently unforeseen, may become apparent upon reviewing the foregoing disclosure. Accordingly, the exemplary implementations set forth above, are intended to be illustrative, not limiting.

What is claimed is:

1. A system for preparing and analyzing genetic material, comprising:
- a microfluidic channel formed in a substrate;
- a first fluid, including at least one target particle and at least one bead and non-target material;
- a microfabricated MEMS fluidic valve, configured to open and close the microfluidic channel and formed in the same substrate wherein the MEMS valve when in the sort position, separates the target particle and redirects the target particle into a first sort channel containing the first fluid;
- a second fluid, immiscible with the first fluid;
- a second microfluidic channel containing the second immiscible fluid
- a nozzle disposed between the first sort channel and the second microfluidic channel, wherein the nozzle forms a droplet comprising a quantity of the first fluid along with the target particle, the quantity determined by the MEMS fluidic valve opening and closing,
- a fluidic manifold that accepts the droplet and lyses the target particle enclosed within the particle to release genomic material; and
- a sequencer that sequences the genomic material.

2. The system of claim 1, further comprising a magnetic bead attached to a barcode, wherein the barcode uses single ended oligonucleotides that are containing predefined sequences, wherein the microfabricated MEMS fluidic valve also separates the magnetic bead and delivers it into the same droplet as the target particle, such that the droplet contains the aqueous fluid, the target particle and the barcoded bead, and flows in a stream of the immiscible second fluid.

3. The system of claim 1, wherein the sequencer is an NGS sequencer, and further comprises a cell lysis and transcription module, and wherein the NGS sequencer sequences at least one of the genomic material and the barcode.

4. The system of claim 2, wherein the sequencer further comprises a cDNA library and a polymerase chain reaction amplification stage.

5. The system of claim 4, wherein the cDNA library comprises adaptors used as a template for rolling circle amplification (RCA).

6. The system of claim 2, wherein the sequencer further comprises a rolling circle amplification stage which produces rolonies.

7. The system of claim 1, wherein the sequencer further comprises: a library preparation stage which prepares a genomic library, and sequences a region of interest from the genomic material using the genomic library.

8. The system of claim 2, wherein the sequencer further comprises a sequencing stage which detects the amino acid sequence of the genomic material by successive application of chemistry reagents and imaging.

9. The system of claim 6, wherein the sequencer further comprises a second microfluidic channel having a functionalized surface, wherein the rolonies adhere to the functionalized surface.

10. The system of claim 1, further comprising an interrogation region in the microfluidic channel; and a laser directed into the laser interrogation region, wherein the laser identifies target particles, and wherein the microfabricated MEMS fluidic valve is configured to separate the target particles from the non-target material in response to a signal from the interrogation region, and direct the target particle into the droplet.

11. The system of claim 1, further comprising:
- a bead disposed in the first fluid, wherein the bead is attached to a plurality of fluorescent tags, wherein the fluorescent tags identify the bead with a fluorescent signal, and wherein the microfabricated MEMS fluidic valve is configured to separate the bead and direct the bead into the droplet, wherein the bead and a target particle, are both located within the same droplet.

12. The system of claim 11, wherein the bead is coupled to the target particle.

13. The system of claim 1, wherein the microfabricated MEMS fluidic valve, moves in a single plane when opening and closing, and wherein that plane is parallel to a surface of the substrate.

14. A process for separating and analyzing a genomic sequence from a target cell, comprising:
- forming a first fluidic channel on a substrate;
- providing a first fluid flowing in the first microfluidic fluid channel;
- opening and closing a microfabricated MEMS fluidic valve, to open and close the microfluidic channel;
- capturing at least one of a target particle and a bead with identifiers disposed thereon;
- providing a source of an immiscible second fluid, immiscible with the first fluid, wherein the immiscible second fluid flows in a second fluidic channel;
- forming a nozzle at the output of the first fluidic channel which dispenses a droplet into the second fluidic channel; and
- dispensing the droplet of the first fluid into the immiscible second fluid, wherein a dimension of the droplet is determined by a timing of opening and closing of the microfabricated microfluidic valve, and wherein the droplet encloses at least one of the bead and the target particle having a genomic sequence, and wherein both the droplet with the quantity of the first fluid and the second immiscible fluid flow within the microfluidic microchannel formed in the substrate; and
- sequencing the genomic material.

15. The method of claim 14, wherein sequencing the genomic material further comprises;
- lysing the target particle to release the genomic material.

16. The method of claim 15, further comprising:
- providing a bead attached to a plurality of fluorescent tags, wherein the fluorescent tags specify the identity of the bead with a fluorescent signal,
- separating the bead using the microfabricated MEMS fluidic valve; and
- directing the bead into the droplet, wherein the bead and the target particle, are located within the same droplet.

17. The method of claim 16, wherein sequencing the genomic material comprises using the cDNA library as a template for rolling circle amplification (RCA).

18. The method of claim 17, wherein the RCA is primed using an oligonucleotide (RCA primers) that is complementary to the common adapter portion of the circularized DNA library.

19. The method of claim 17, wherein the template is recognized by the polymerase performing the RCA which amplifies the DNA regardless of the target sequence into DNA rolonies containing several hundred copies or concatemers of the DNA.

20. The method of claim 19, further comprising loading the rolonies into a microfluidic channel;

Immobilizing the rolonies on a functionalized glass surface; and sequentially applying reagents to discern the sequence of the genomic material.

* * * * *